Jan. 1, 1952 F. W. ANDERSON Plant Pat. 1,060

NECTARINE TREE

Filed Nov. 7, 1950

WITNESS

Addison E. Avery

INVENTOR

Frederic W. Anderson

Webster & Webster

ATTYS

Patented Jan. 1, 1952

Plant Pat. 1,060

UNITED STATES PATENT OFFICE 1,060

NECTARINE TREE

Frederic W. Anderson, Merced, Calif., assignor to Kim Brothers, a partnership doing business as Reedley Nursery, Reedley, Calif.

Application November 7, 1950, Serial No. 194,459

1 Claim. (Cl. 47—62)

This invention relates to a new and distinct variety of nectarine tree which bears large, yellow-fleshed clingstone fruit; the variety being the result of a continuing breeding program which I am carrying forward to obtain more commercially desirable nectarines.

The herein described variety of nectarine tree has close resemblance to the Le Grand nectarine (United States Plant Patent 549), but the present variety is distinctive in comparison thereto in that it bears fruit having an exterior color which is a much more intense or brighter red, and a ripening period approximately one week earlier.

This new and distinct variety of nectarine tree was originated by me upon my ranch near Merced, county of Merced, State of California, in the following manner:

In early March of 1942 all of the blooms on one Le Grand nectarine tree were pollenized with pollen from a Kim nectarine tree (United States Plant Patent No. 173).

Seed from the resulting fruit was planted during the following winter, and in excess of one hundred seedlings were obtained. The seedlings of vigorous and healthy appearance were then topworked on orchard trees and these have all borne yellow-fleshed fruit. Among these, the instant variety appeared and was immediately recognized by me as being distinctive, and advantageous marketwise, because of its unusually bright red color, and its ripening period earlier than the Le Grand nectarine.

Since its discovery the new variety has been successfully asexually reproduced, with the reproductions carrying forward all of the distinctive characteristics of the parent and its fruit. Such reproduction was accomplished as follows:

To determine that true, asexual reproduction could be attained, and to fix the ripening period of the new variety more exactly, it was topworked during the summer of 1947 on two separate orchard trees, along with Gower, Quetta, and Le Grand nectarines. These bore fruit during the 1949 and 1950 seasons, and during both seasons the instant variety ripened approximately five days after the Gower and approximately five days earlier than the Le Grand and Quetta.

The fruit of the herein claimed variety colors and ripens uniformly, so that harvest can be completed—from trees of the same age and in the same orchard—before the Le Grand and Quetta harvest begins. Harvest of the instant variety will follow very closely after completion of harvest of the Early Le Grand variety (United States Plant Patent 980); thus filling the gap in the harvesting period between said Early Le Grand nectarine and the Le Grand nectarine, with a nectarine of the same general characteristics.

Figure 1:
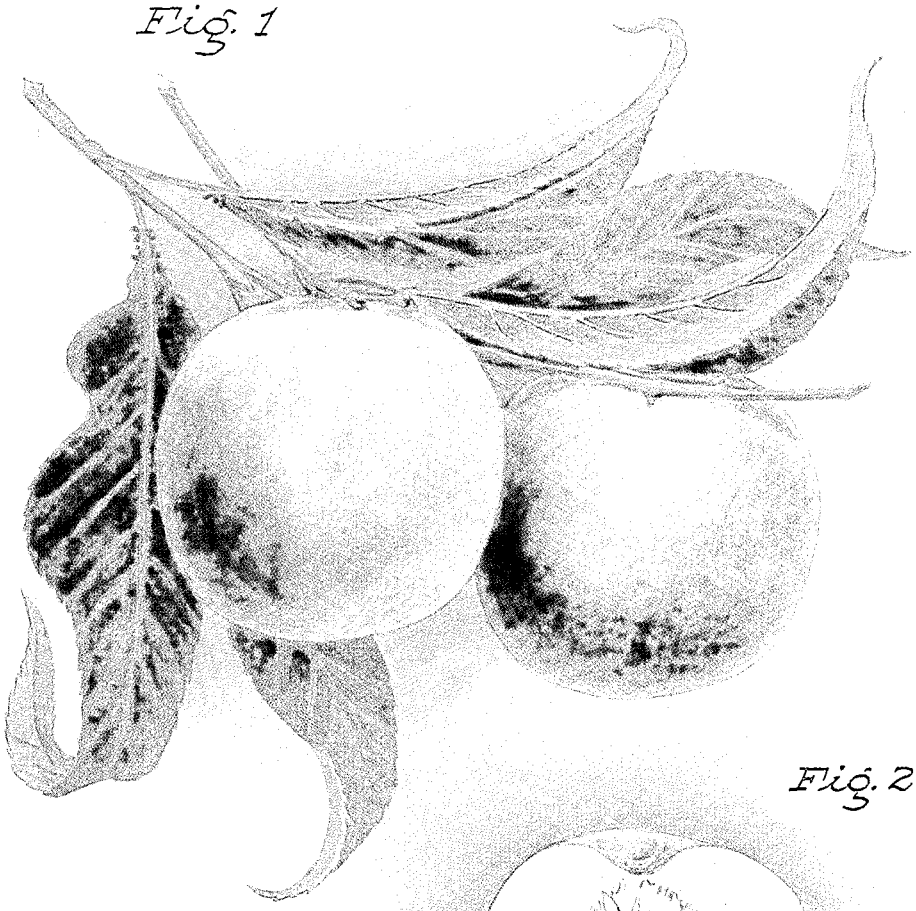
Fig. 1 is a perspective view of fruit of the new variety in connection with stems and leaves.
Figure 2:
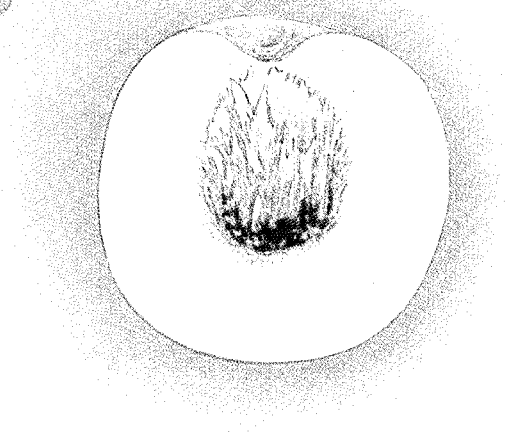
Fig. 2 is a sectional view of one of the fruits with the stone exposed.

Referring now more specifically to the pomological details of the new and distinct variety of nectarine tree, the following is an outline description thereof; all major color plate identifications being by reference to Maerz and Paul Dictionary of Color.

Tree: Large; vigorous; spreading; productive bearer; regular bearer.

Trunk: Stocky.

Branches: Stocky. Above medium size. *Lenticels*—medium number; medium size.

Leaves: Average length, 6″ to 7″; average width, 1¾″ to 2″. Large size; smooth. Color—medium green (22–L–6) on top side; lighter green (21–K–5) tending to yellowish on under side.

*Leaf stems.*—Color—light green (19–K–3).

*Margins.*—Crenate.

*Petiole.*—Medium length; medium thickness.

*Glands.*—Average number, about four. Alternate; medium size; reniform. Usually located two on the petiole and two or more on the margins of the blade.

*Stipules.*—None.

Flower buds: Medium size; plump.

Flowers: Large size; pink; showy, opening about with the Elberta peach. *Anthers*—red in color, producing viable pollen, so that the variety is self-fruitful.

Fruit:

*Size.*—Large for a nectarine, being considerably larger than the Quetta variety, and about the same size as the Le Grand variety. Well grown specimens average 3″ in diameter from cheek to cheek and average 3″ from stem to apex, and are quite uniform in size.

*Ripens.*—Uniformly—comparable to the J. H. Hale peach and the Le Grand nectarine.

*Shape.*—Globose.

*Suture.*—Shallow with slight depression beyond the pistil point.

*Ventral surface.*—Rounded, with equal sides.

*Cavity.*—Rounded. Average diameter ⅜″; average breadth ¾″. Marking—usually completely covered with red.

*Base.*—Flat.
*Apex.*—Slightly depressed, with point almost lacking.
*Stems.*—Stout. Adhere strongly to stone.

Skin: Thick; tough; tenacious to flesh.
*Color.*—Yellow (9–I–8) under-color; completely overspread with bright red (3–L–6 shading to 5–L–6).
*Pubescence.*—None.

Flesh:
*Color.*—Yellow (10–J–7), with considerable red (4–J–4) next to the stone.
*Amagydaline.*—Moderate.
*Juice.*—Abundant.
*Fibers.*—Abundant.
*Texture of flesh.*—Firm.
*Ripens.*—Evenly.
*Flavor.*—Delicate.
*Aroma.*—Distinct.
*Eating quality.*—Good.

Stone: Cling.
*Fingers.*—Long.
*Size.*—Large. Average length, $1\frac{5}{16}''$; average breadth, $1\frac{1}{4}''$; average thickness, $\frac{3}{4}''$.
*Form.*—Round to oval.
*Base.*—Oblique.
*Hilum.*—Broad; oval.
*Apex.*—Rounded.
*Sides.*—Equal.

*Surface.* — Irregularly furrowed; pitted throughout.
*Ventral side.*—Thick.
*Dorsal side.*—Full with deep grooves.
*Ridges.*—Continuous.
*Color.*—Reddish purple (55–L–12).
*Tendency to split.*—Very little.

Resistance to insects and diseases: Approximately the same as other commercial nectarine varieties, and is controlled by the same spray program.

Keeping and shipping qualities: Very good, having very firm flesh.

Eating quality: Excellent.

The tree and its fruit herein described may vary in slight detail due to climatic and soil conditions under which the variety may be grown.

Having thus described my invention, I claim:

A new and distinct variety of nectarine tree, substantially as described and illustrated, bearing fruit which, in comparison to the Le Grand, is of brighter red color, with a ripening period five days to a week earlier; the tree and its fruit otherwise being quite similar to the Le Grand, including large, firm-fleshed, uniformly ripening fruit.

FREDERIC W. ANDERSON.

No references cited.